United States Patent [19]

Burstein et al.

[11] 4,298,992
[45] Nov. 10, 1981

[54] POSTERIORLY STABILIZED TOTAL KNEE JOINT PROSTHESIS

[75] Inventors: Albert H. Burstein, Greenwich, Conn.; John N. Insall, Scarsdale, N.Y.

[73] Assignee: New York Society for the Relief of the Ruptured and Crippled, New York, N.Y.

[21] Appl. No.: 113,632

[22] Filed: Jan. 21, 1980

[51] Int. Cl.³ .................................................. A61F 1/03
[52] U.S. Cl. .................................... 3/1.911; 128/92 C
[58] Field of Search ........................ 3/1.911; 128/92 C

[56] References Cited

U.S. PATENT DOCUMENTS

| | | | |
|---|---|---|---|
| 3,694,821 | 10/1972 | Moritz | 3/1.911 |
| 3,824,630 | 7/1974 | Johnston | 128/92 C X |
| 3,840,905 | 10/1974 | Deane | 3/1.911 |
| 4,209,861 | 7/1980 | Walker et al. | 3/1.911 |
| 4,213,209 | 7/1980 | Insall et al. | 3/1.911 |
| 4,224,697 | 9/1980 | Murray et al. | 3/1.911 |

Primary Examiner—Clifford D. Crowder
Attorney, Agent, or Firm—Brumbaugh, Graves, Donohue & Raymond

[57] ABSTRACT

A box-like recess between the condylar portions of the femoral component has a transverse convexly curved cam follower portion at the posterior extremity of a superior wall which engages a concave cam surface at the inferior portion of the posterior surface of a tibial post that extends up from the plateau surface of the tibial component into the recess. The camming action between the cam follower and cam surface forces the zones of contact between the condylar portions of the femoral component and concavities in the tibial component posteriorly as the leg approaches full flexion, thereby increasing the range of flexion without interference between posterior surfaces of the femur and the tibial component and preventing anterior dislocation of the femur. The plateau of the tibial component slopes inferiorly and posteriorly, also to increase the range of flexion without interference.

4 Claims, 12 Drawing Figures

POSTERIORLY STABILIZED TOTAL KNEE JOINT PROSTHESIS

FIELD OF THE INVENTION

The present invention relates to knee joint prostheses and, in particular, to an implantable knee joint prosthesis which replaces all surfaces of the femur and tibia which engage each other at the knee joint and stabilizes joint function in leg flexion.

BACKGROUND OF THE INVENTION

Researchers at the Hospital for Special Surgery, New York, N.Y. (the assignee of the present invention) have been working for many years on the development of prosthetic joints, including the knee joint. Developments in prosthetic knee joints have come to focus on "total" prostheses in which all contacting surfaces of the femur and tibia are replaced by surfaces of the femoral and tibial components of the prosthesis and on "stabilized" prostheses in which parts of the components, such as hinge pins or balls and sockets, control the motion. In general, the total knee prostheses currently used allow antero-posterior translation, lateral angulation and rotation in much the same way as the anatomical knee joint does and rely on the tendons and ligaments to impart stability. In some cases, however, the soft tissue is inadequate for one reason or another to provide the required stability, and the prosthesis is highly subject to dislocation and therefore of impaired usefulness in restoring normal function.

Hinge and ball and socket type knee joint prostheses generally fail to reproduce the motions of the anatomical joint. For that reason, they are not considered desirable, except for patients having inadequate soft tissue in the knee joint to provide stability, because normal function is not restored—the joint functions abnormally. Moreover, reliance on the mechanics of the prosthesis for stability places considerable strain on the prosthesis, and failure by dislodgment of the components is much much more prevalent with stabilized prostheses than with total prostheses.

U.S. Pat. No. 4,213,209 issued July 22, 1980 for "KNEE JOINT PROSTHESIS" (owned by the assignee of the present invention), describes and shows a knee joint prosthesis which can be characterized as a hybrid of the total and stabilized types. It has the attribute of providing generally normal function characteristic of total prostheses and the attribute of limiting certain excessive relative motions characteristic of stabilized prostheses.

SUMMARY OF THE INVENTION

The present invention provides certain improvements in the knee joint prostheses of U.S. Pat. No. 4,213,209 (referred to above). The prosthesis, according to the present invention, shares several features and principles with the one to which that application is directed. Thus, it comprises a femoral component having a pair of laterally spaced-apart condylar portions, each of which has an external surface that is smoothly convexly curved antero-posteriorly to match generally the lateral profile of the anatomical femoral condyle and smoothly convexly curved lateraly throughout its antero-posterior extent. A box-like structure connects the condylar portions and defines an intercondylar recess which opens inferiorly toward the tibia. The tibial component has a platform portion having laterally spaced-apart concavities, each of which receives one of the condylar portions of the femoral component. A post extends superiorly from the tibial plateau into the intercondylar recess of the femoral component. To the extent described thus far, the present invention allows relative motions (antero-posterior translation, lateral angulation and rotation) closely resembling those of the anatomical joint and some total prosthetic joints and limits excessive motions by engagement between the tibial post and femoral recess. Those features it shares with the prosthesis of U.S. Pat. No. 4,213,209.

The principal improvements of the present invention are:

(1) a transverse, convex cam follower portion at the posterior extremity of the superior wall of the femoral intercondylar recess engages a concave cam surface at the inferior, posterior portion of the tibial post at and near full flexion and forces the zones of contact between the femoral condylar portions and the tibial concavities posteriorly as flexion approaches full;

(2) the tibial plateau slopes inferiorly and posteriorly;

(3) the superior wall of the femoral recess is generally flat and slopes only slightly antero-inferiorly, relative to a nominal base plane, and does not engage the tibial post except under a relatively high amount (say, 15 degrees) of hyper-extension.

The modifications alter several aspects of the function of the prosthesis and provide several advantages. Among the more important are the following:

(1) the camming action between the tibial post and the femoral intercondylar recess that occurs near and at full flexion occurs at a region close to the tibial plateau-leverage tending to cause dislodgment of the tibial component is minimized.

(2) The camming action near and at full flexion makes the femoral component "ride" posteriorly on the tibial component, thereby increasing the range of flexion without interference between posterior surfaces of the femoral condyle and the posterior extremity of the tibial component.

(3) The postero-inferior slope of the tibial plateau likewise increases the range of flexion by lowering the posterior extremity of the tibial plateau while still retaining height at the anterior extremity for good "nesting" of the femoral condyles in the tibial concavities at extension and the consequential stabilizing effect of nesting at extension, especially stability against anterior displacement of the femur.

(4) Generally, the knee joint (both an anatomical and a prosthetic) is inherently stable at extension when the patient is standing—the nesting of the femoral condyles on the tibial plateau, the weight of the body generally centered over the knees and the status of the ligaments and tendons are all favorable to knee joint stability. It is, therefore, generally superfluous for the prosthetic joint to provide extra stability by engagement between the tibial post and femoral intercondylar recess at extension.

(5) The generally horizontal superior wall (roof) of the femoral intercondylar recess facilitates implantation of the tibial component by allowing plenty of room for the surgeon to insert the tibial component between the then implanted femoral component and the exposed tibia and then push it down into place.

(6) Under hyper-extension joint stability is diminished—the invention provides stability against posterior dislocation of the femur under hyper-extension by engagement between the anterior wall of the post and the anterior portion of the roof of the recess.

For a better understanding of the invention reference may be made to the following description of an exemplary embodiment, taken in conjunction with the figures of the accompanying drawings.

DESCRIPTION OF THE EMBODIMENT

Figure 1:
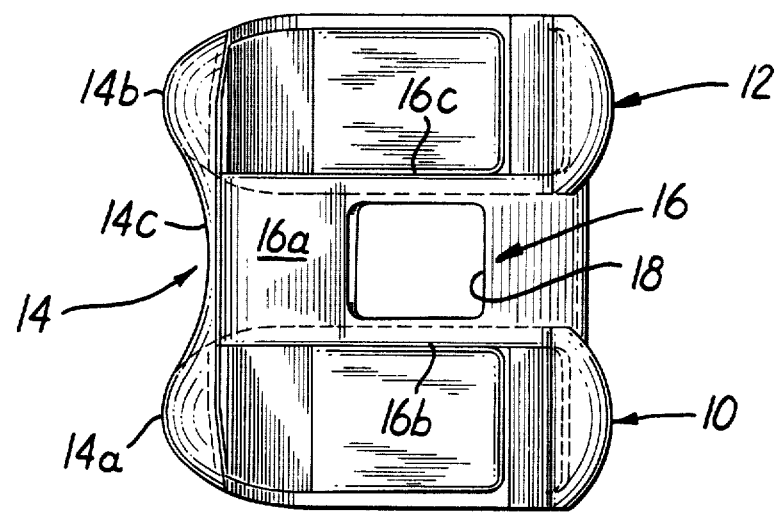
FIGS. 1, 2 and 3, are plan, side elevational, and rear elevational views, respectively, of the femoral component.
Figure 2:
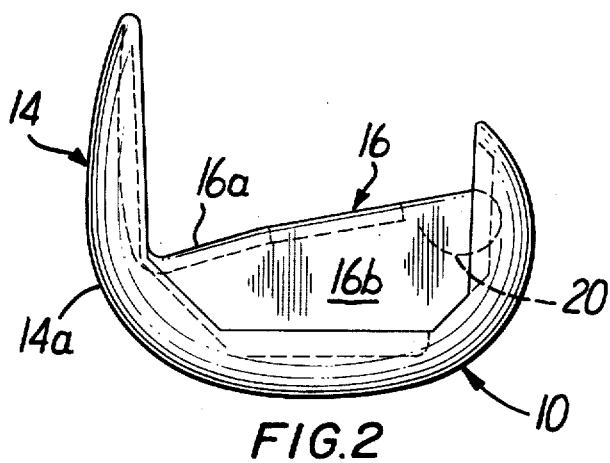

The femoral component comprises a pair of identical laterally spaced-apart femoral condylar portions 10 and 12, each of which is smoothly convexly curved in lateral profile generally to match the curvature of an anatomical femoral condyle and is laterally convexly curved entirely along its antero-posterior extent. The anterior parts of the condylar portions merge smoothly with convexly curved lateral portions 14a and 14b of a patellar portion 14, the medial part 14c of which is laterally concave and inferosuperiorly convex and intersects at its inferior extremity a superior wall or roof 16a of a box-like intercondylar portion 16 which, together with patellar portion 14, connects the condylar portions. A pair of laterally spaced-apart side walls 16b and 16c of the recess join the edges of the roof 16a to the internal edges of the condylar portions. A hole 18 in the roof of the intercondylar portion 16 allows fluids and tissue more readily to enter and grow into the recess defined by the intercondylar recess for better intergration of the component with anatomical structures and systems.

The surfaces of the femoral component which face the femur are generally flat and, in the case of the "facets" of each condylar portion 10 and 12, are bounded by a small rib or flange, thus to provide a keying effect which holds the component securely on the cement used to attach the component to the femur.

Figure 3:
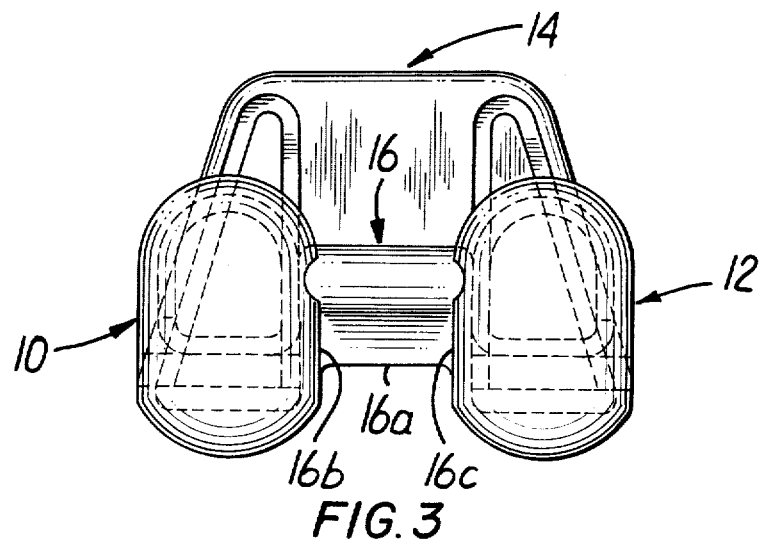

The roof 16a of the intercondylar recess 16 is generally flat (though it does have a slight break between two flat surfaces) and, though generally horizontal (parallel to a nominal base plane), slopes postero-superiorly toward a transverse, convex cam follower surface 20 at the posterior extremity. The notches on the internal edges of the posterior parts of the condylar portions (FIG. 3) are there for a purpose relating to the surgical technique and do not have anything to do with the anatomical structure or function of the prosthesis. The femoral component is preferably made of a surgical grade, durable metal, such as a 316L stainless steel or a chrome-cobalt-molybdenum alloy meeting ASTM Standard #F75-74. All surfaces which are external to the bone are highly polished. The femoral component is symmetrical about a vertical antero-posterior center plane, so it can be used on either knee.

Figure 4:
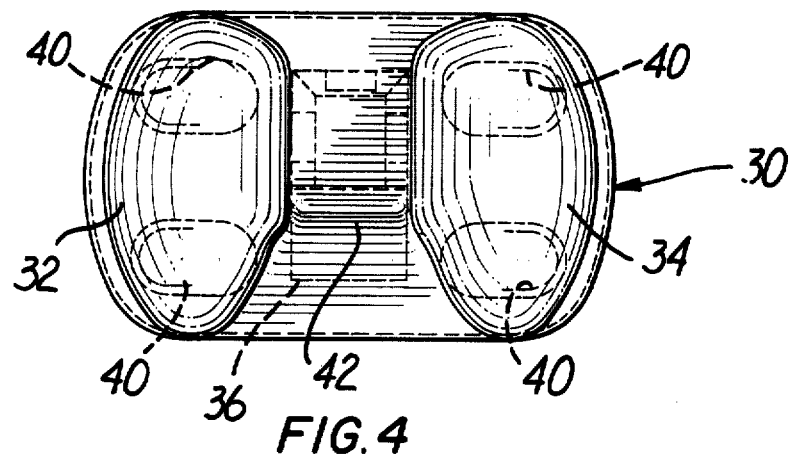
FIGS. 4, 5 and 6 are plan, side elevational and rear elevational views of the tibial component.
Figure 5:
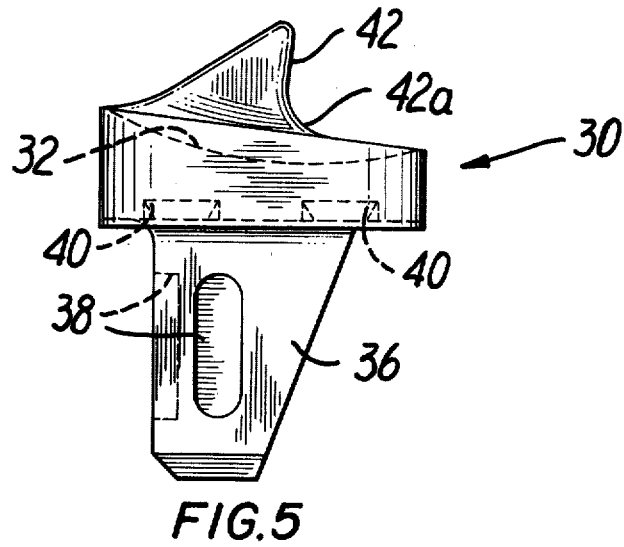
Figure 6:
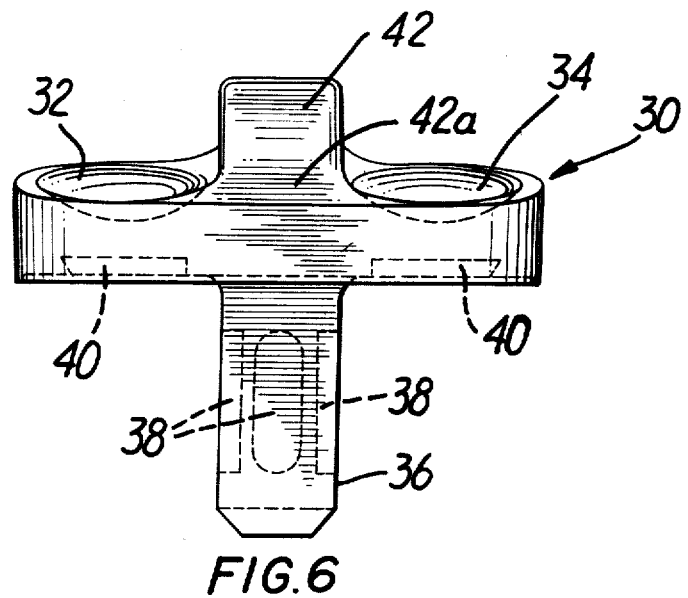

The tibial component (FIGS. 4 to 6) is preferably made of a surgical grade, low-friction, high density, low wearing plastic, such as RCH-1000, and is also symmetrical about a vertical antero-posterior center plane for right or left use. It comprises an oblong, rounded, disc-like plateau portion 30, the upper surface of which is generally flat and slopes down from front to back. Each of a pair of laterally spaced-apart, oblong concavities 32 and 34 receives one of the femoral condylar portions; the "nested" support of the femoral component stabilizes the prosthetic joint but still permits antero-posterior translation, lateral angulation and rotation, all of which are involved in normal function of the anatomical knee joint. The lateral curvature is slightly greater than the lateral curvature of the femoral condylar portions.

A keel-like fixation post 36 extends from the inferior surface of the plateau portion. Cement intrudes into slots 38 in the walls of the fixation post and slots 40 on the inferior surface of the plateau portion and anchors the tibial component to the cement.

A stabilizing post 42 extends superiorly from the plateau portion between the concavities and is received in the femoral intercondylar recess 16. The post 42 is generally triangular in lateral profile and has flat, parallel lateral surfaces, a concave cam surface 42a at the inferior part of the posterior surface, and an anterior surface which slopes anteriorly and superiorly at an acute included angle to a nominal reference plane perpendicular to the nominal axis of the extended leg. The lateral surfaces of the stabilizing post 42 are in sufficient clearance from the lateral walls of the femoral intercondylar recess to allow normal lateral angulation and rotation of the prosthetic knee joint.

Figures 7A, 7B, 7C:
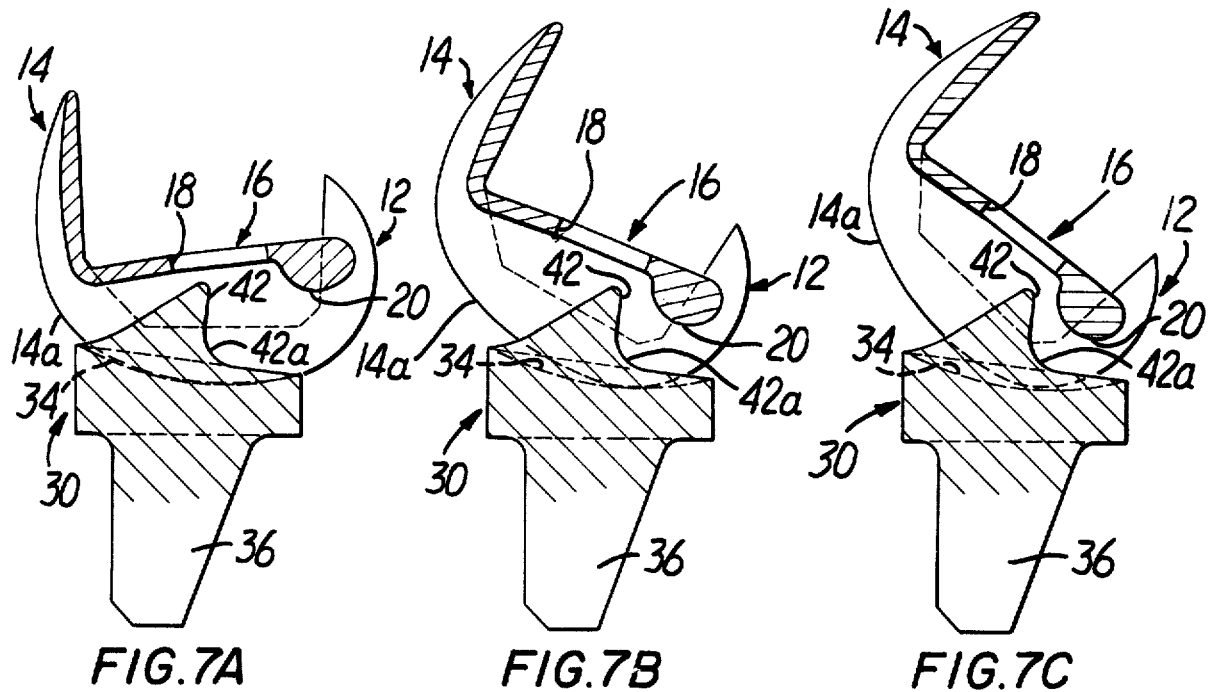
FIGS. 7A to 7F are side cross-sectional views in generally schematic form showing the assembled components in various positions (corresponding to a range of leg articulation from full extension to full flexion).
Figures 7D, 7E, 7F:
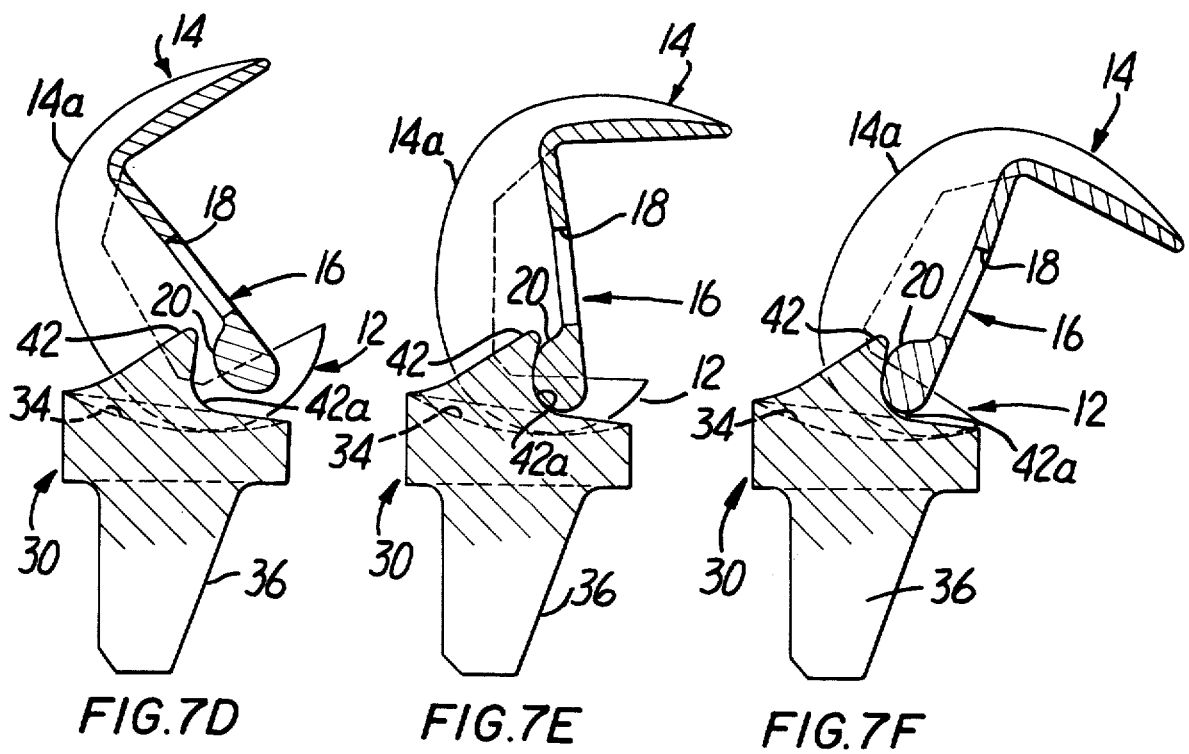

With the leg extended (FIG. 7A) a generally stable position is established by nesting of the femoral condyles in the tibial plateau concavities; the tibial stabilizing post 42 and femoral recess 16 do not engage in the antero-posterioral direction. Under moderate degrees of flexion (FIGS. 7B and 7D) the post and recess continue to remain functionally dormant, but as flexion increases, the greater is the tendency for the femoral cam follower 20 to engage the posterior surface of the tibial post 42, should the hamstring muscles of the thigh pull the tibia backward and tend to dislocate it posteriorly. Somewhere around 40° to 50° flexion (FIG. 7E) the femoral cam follower 20 should ordinarily engage the tibial cam surface 42a and as flexion increases beyond that point will force the prosthetic femoral condyles to roll back in the tibial concavities (FIG. 7F) observe that the zone of contact between the condyles and the concavities shifts posteriorly (compare FIGS. 7E and 7F) to a location very close to the posterior extremity of the tibial plateau at full flexion. This shift and the sloping of the tibial plateau allows a high flexion to occur without interference between the posterior extremity of the femur and the posterior extremity of the tibial component. The post and recess thus stabilize joint functions near and at full flexion by controlling the relative antero-posterior positions of the femur and preventing anterior translation.

If the knee should undergo a fairly large hyperextension (not shown, but see FIG. 7A), say about 15°, the anterior part of the superior wall 16a of the femoral recess 16 will roll back into engagement with the anterior surface of the tibial post and prevent posterior dislocation of the femur.

We claim:
1. In a knee joint prosthesis having
   a femoral component which includes a pair of laterally spaced-apart condylar portions, each of which has an external surface which is smoothly convexly curved antero-posteriorly to match generally the lateral profile of an anatomical femoral condyle and smoothly convexly curved laterally throughout its antero-posterior extent, and a box-like intercondylar portion joining the condylar portions; and a tibial component which includes a plate-like platform portion having on its superior surface a pair of laterally spaced-apart concavities, each of which is adapted to receive in nested relation one of the condylar portions of the femoral component, and a post extending superiorly from the platform surface intermediate the concavities for reception in the intercondylar portion of the femoral component;

the improvements wherein:

the intercondylar portion defines a recess opening inferiorly toward the tibial component and includes spaced-apart lateral walls, a superior wall which joins the lateral walls and has an inferior surface that is generally flat, lies generally parallel to a reference plane perpendicular to the nominal axis of the extended leg and intersects a patella portion of the femoral component at a location that is substantially above the platform portion of the tibial component and generally level with the top of the tibial post at full extension, and a cam follower portion at the posterior end of the superior wall having a transverse convexly curved follower surface; and the tibial post has a posterior surface having a concavely curved cam portion adjacent the juncture between the post and the platform surface, the cam portion on the post being adapted to be ordinarily engaged by the follower surface on the intercondylar portion only after about 40° to 50° flexure of the leg and a tendancy of the femur to translate anteriorly relative to the tibia and to force the zones of contact between the femoral condylar surfaces of the femoral component and the concavities of the tibial component posteriorly as the degree of leg flexion increases.

2. A knee joint prosthesis according to claim 1 wherein the tibial post is generally triangular in lateral profile and includes a generally flat anterior surface lying obliquely at an acute angle to said reference plane, the anterior surface of the tibial post being engageable by an anterior part of the inferior surface of the superior wall of the intercondylar recess of the femoral component only upon hyper-extension of the leg and not otherwise.

3. A knee joint prosthesis according to claim 1 wherein an anterior portion of the inferior surface of the superior wall of the recess of the femoral component slopes at a small acute angle inferiorly and anteriorly thus to afford engagement with the anterior surface of the post of the tibial component upon, and only upon about 15° of hyper-extension of the leg.

4. A knee joint prosthesis according to claim 1 wherein the superior surface of the tibial component slopes inferiorly and posteriorly relative to the reference plane, thus to permit a high degree of flexion of the leg without interference between the anatomical femur and the posterior portion of the tibial component.

* * * * *